US010946005B2

(12) United States Patent
Moraitis

(10) Patent No.: US 10,946,005 B2
(45) Date of Patent: Mar. 16, 2021

(54) METHODS FOR SHRINKING PITUITARY TUMORS

(71) Applicant: Corcept Therapeutics Incorporated, Menlo Park, CA (US)

(72) Inventor: Andreas Moraitis, Sunny Isles Beach, FL (US)

(73) Assignee: Corcept Therapeutics Incorporated, Menlo Park, CA (US)

( * ) Notice: Subject to any disclaimer, the term of this patent is extended or adjusted under 35 U.S.C. 154(b) by 0 days.

(21) Appl. No.: 16/678,988

(22) Filed: Nov. 8, 2019

(65) Prior Publication Data

US 2020/0147065 A1 May 14, 2020

Related U.S. Application Data

(60) Provisional application No. 62/758,477, filed on Nov. 9, 2018.

(51) Int. Cl.
*A61K 31/444* (2006.01)
*A61P 35/00* (2006.01)
*A61N 5/10* (2006.01)
*A61B 17/3205* (2006.01)

(52) U.S. Cl.
CPC ............ *A61K 31/444* (2013.01); *A61P 35/00* (2018.01); *A61B 17/3205* (2013.01); *A61N 5/10* (2013.01)

(58) Field of Classification Search
CPC .............................. A61K 31/444; A61P 35/00
See application file for complete search history.

(56) References Cited

U.S. PATENT DOCUMENTS

| | | |
|---|---|---|
| 8,859,774 B2 | 10/2014 | Hunt et al. |
| 9,273,047 B2 | 3/2016 | Hunt et al. |
| 9,707,223 B2 | 7/2017 | Hunt et al. |
| 9,956,216 B2 | 5/2018 | Hunt et al. |
| 2015/0080389 A1 | 3/2015 | Hunt et al. |
| 2018/0125856 A1 | 5/2018 | Moraitis et al. |

FOREIGN PATENT DOCUMENTS

WO 2017151613 A1 9/2017

OTHER PUBLICATIONS

Check et al., "Evidence that Mifepristone, a Progesterone Receptor Antagonist, Can Cross the Blood Brain Barrier and Provide Palliative Benefits for Glioblastoma Multiforme Grade IV" Anticancer Research 34: 2385-2388 (2014).
Check et al., "Mifepristone Causing Complete Remission of Rapidly Advancing Leukemia with Measurement of Progesterone-induced Blocking Factor" Anticancer Research 34: 2413-2416 (2014).
Fleseriu, et al., "Mifepristone, a Glucocorticoid Receptor Antagonist, Produces Clinical and Metabolic Benefits in Patients with Cushing's Syndrome" *J. Clin Endocrin Metab* 97(6):2039-2049 (Jun. 2012).
Fleseriu et al., "Changes in Plasma ACTH Levels and Corticotroph Tumor Size in Patients With Cushing's Disease During Long-term Treatment With the Glucocorticoid Receptor Antagonist Mifepristone" J Clin Endocrinol Metab 99(10):3718-3727 (Oct. 2014).
Hunt et al., "Identification of the Clinical Candidate (R)-(1-(4-Fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone (CORT125134): A Selective Glucocorticoid Receptor (GR) Antagonist" J. Med. Chem. 60:3405-3421 (2017).
Kovacs et al. "Glucocorticoid Receptor Expression in Nontumorous Human Pituitaries and Pituitary Adenomas" Endocrine Pathology (11:3):267-275 (2000).
Terzolo et al., "Tumor Shrinkage with Preoperative Relacorilant Therapy in Two Patients with Cushing Disease Due to Pituitary Macroadenomas" Control/Tracking No. 2019-A-6692-ENDO, ENDO Abstract for 2019 Annual Meeting (Mar. 23-26, 2019).
Touat et al., "Successful treatment of multiple intracranial meningiomas with the antiprogesterone receptor agent mifepristone (RU486)" Acta Neurochir (2014) 156:1831-1835.
Winters, et al., "Addison's Disease and Pituitary Enlargement," The American Journal of the Medical Sciences, Jun. 2015, 349(6):526-529.
Cuevas-Ramos et al., "Treatment of Cushing's Disease: A Mechanistic Update", Journal of Endocrinology, vol. 223, No. 2, 2014, R19-39.
Hunt et al., "Assessment of Safety, Tolerability, Pharmacokinetics, and Pharmacological Effect of Orally Administered CORT125134: An Adaptive, Double-Blind, Randomized, Placebo-Controlled Phase 1 Clinical Study", Clinical Pharmacology in Drug Development, vol. 7, No. 4, May 2018, pp. 408-421.
PCT/US2019/060548 , "International Search Report and Written Opinion", dated Apr. 10, 2020, 11 pages.

*Primary Examiner* — Samira J Jean-Louis
(74) *Attorney, Agent, or Firm* — Kilpatrick Townsend & Stockton LLP

(57) ABSTRACT

Pituitary tumors may be reduced in size by administration of relacorilant. Pituitary tumors include, without limitation, non-secreting tumors, hormone-secreting tumors, adenomas, and carcinomas. Relacorilant administration may be effective to reduce hormone secretion from a hormone-secreting pituitary tumor, e.g., to reduce adrenocorticotrophic hormone (ACTH) secretion. A pituitary tumor may be imaged before and/or after relacorilant administration. Relacorilant may be administered independent of surgery, and before, during, or after surgery to treat a pituitary tumor. Relacorilant may aid or improve surgical outcomes, and may reduce the size or growth of pituitary tumor tissue before surgery, and any tumor tissue remaining following surgical treatment.
Relacorilant may be orally administered for the treatment of pituitary tumors. Relacorilant may be orally administered to a fasted patient, or to a fed patient. Relacorilant may be administered in conjunction with other pituitary tumor targeting treatments, including surgical treatments, radiation treatments, chemotherapy for carcinomas, and other pharmaceutical treatments.

30 Claims, 3 Drawing Sheets

Pre-Treatment MRI

Post-Treatment MRI

Pre-Treatment MRI

Post-Treatment MRI

Pre-Treatment MRI

Post-Treatment MRI

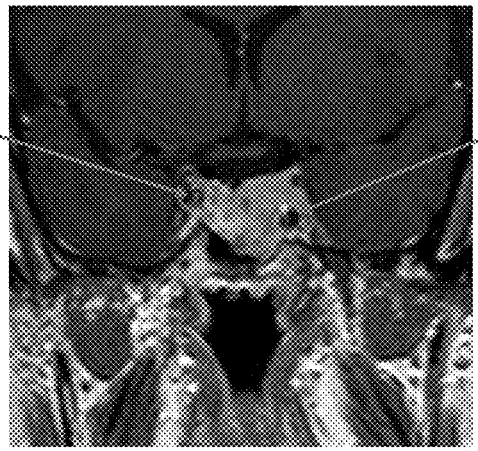
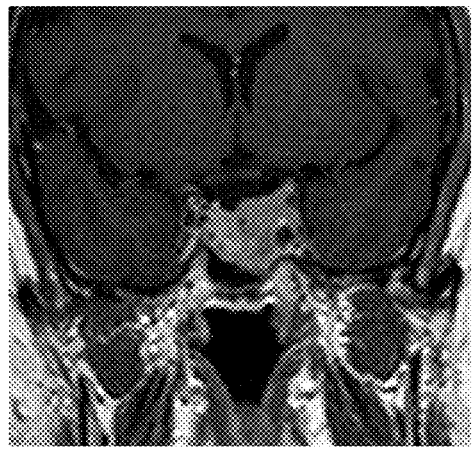
Pre-Treatment  Post-Treatment
FIG. 3A  FIG. 3B
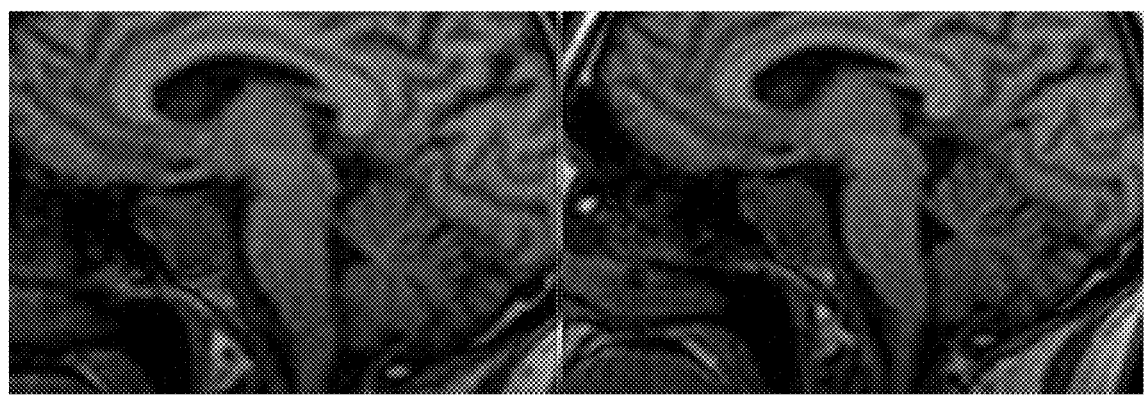
Pre-Treatment  Post-Treatment
FIG. 3C  FIG. 3D

METHODS FOR SHRINKING PITUITARY TUMORS

CROSS-REFERENCE TO RELATED APPLICATION

This application claims, under 35 U.S.C. § 119(e), priority to and the benefit of U.S. Provisional Patent Application Ser. No. 62/758,477, filed Nov. 9, 2018, the entire contents of which application is hereby incorporated by reference in its entirety.

BACKGROUND

The pituitary gland, under the control of the hypothalamus, secretes hormones that affect myriad bodily functions. It is situated in the sella turcica, outside the blood-brain barrier (BBB), and comprises an anterior portion, the adenohypophysis; an intermediate portion (rudimentary in humans); and a posterior portion, the neurohypophysis. The pituitary gland is connected to the hypothalamus of the brain via the pituitary stalk (infundibulum) of the neurohypophysis. The adenohypophysis endocrine cells secrete hormones, including adrenocorticotrophic hormone (ACTH), prolactin (PRL), growth hormone (GH), thyroid stimulating hormone (TSH), follicle stimulating hormone (FSH), luteinizing hormone (LH), melanocyte stimulating hormone (MSH), β-lipotropin, and others. The neurohypophysis secretes the peptide hormones oxytocin and vasopressin (antidiuretic hormone, ADH).

Cushing's syndrome is a debilitating chronic disease caused by high levels of cortisol, and characterized by high blood sugar, high blood pressure, weight gain (including a characteristic "hump" on the neck or back), hirsuteness, depression, and other symptoms. Cortisol is produced in the adrenal glands in response to ACTH; in some cases of Cushing's syndrome, excess cortisol is caused by adrenal abnormalities (e.g., an adrenal tumor). In other cases, the excess cortisol is due to excess ACTH secretion from the pituitary gland that acts on the adrenal glands to produce the excess cortisol. Such excess pituitary ACTH secretion is typically caused by a pituitary tumor. When excess pituitary ACTH secretion causes the excess cortisol, the disorder is termed "Cushing's Disease".

Pituitary tumors may be non-functional (i.e., non-hormone secreting) or may be hormone-secreting tumors. Pituitary tumors are typically adenomas (benign, non-cancerous tumors), including macroadenomas and microadenomas, which may be, e.g., corticotrophs, somatotrophs, lactotrophs, or gonadotrophs (Kovacs et al., *Endocrine Pathology* 11(3):2670275 (2000)). First-line treatment for Cushing's Disease typically involves surgery to remove the pituitary tumor; however, in many cases, the patient is unable to undergo surgery, or not all of the tumor is able to be resected (e.g., if the tumor has invaded cranial regions outside the sella turcica, or has invaded bone, or for other reasons), or it may grow back, or may have metastasized. In some cases, radiation treatment is applied, e.g., following surgery. Conventional chemotherapy treatment often used for other tumors may be inapplicable for pituitary tumors, or may not be suitable for patients suffering from pituitary tumors.

Medical treatment to reduce cortisol production has been prescribed to treat Cushing's syndrome. Medical treatment to reduce the effects of excess cortisol is often administered, particularly when symptoms persist following surgery (e.g., mifepristone (prescribed as)KORLYM®; see also U.S. Pat. No. 9,956,216). However, surgery, radiation and standard chemotherapy may be incompletely effective, and may have severe side-effects, which may make them unsuitable for Cushing's patients. Thus, medical (i.e., non-surgical) treatments for pituitary tumors which cause Cushing's Disease remain lacking.

Accordingly, new medical treatments for pituitary tumors are required, including new medical treatments for pituitary tumors causing Cushing's Disease are required.

SUMMARY

Applicant discloses herein that administration of relacorilant may be effective to shrink (i.e., reduce the size of) a pituitary tumor. In embodiments, the pituitary tumor to be shrunken by administration of relacorilant is visible using clinical imaging techniques. In embodiments, the methods include selecting a patient suffering from a pituitary tumor that is visible, and which may be measurable, using clinical imaging techniques. In embodiments, the patient suffers from a symptom of Cushing's syndrome. In embodiments, the patient suffers from Cushing's Disease. In embodiments, the methods include selecting a patient for whom the present methods are suitable, and in embodiments, for whom the present methods are preferable to other methods, whether provided as first line treatment, or in conjunction with other treatments. Accordingly, Applicant discloses herein new and surprising treatment methods directed to patients suffering from pituitary tumors. These novel methods may be the sole treatment used to treat pituitary tumors, and may also be used along with other treatments, including surgical treatments, radiation treatment, and other treatments.

The pituitary tumor to be treated (i.e., shrunk) may be a non-functional (non-secreting) tumor, a hormone-secreting tumor, a benign tumor, or a malignant tumor, with or without metastasis. The pituitary tumor is typically not a non-pituitary metastatic tumor. However, in embodiments, the pituitary tumor may be an invasive tumor. Thus, the pituitary tumor to be treated may be an adenoma or carcinoma, a non-functional (non-secreting) tumor, a hormone-secreting tumor (e.g., a hormone-secreting neuroendocrine tumor), or other tumor. In embodiments, the pituitary tumor to be treated is a pituitary adenoma. In embodiments, the pituitary adenoma to be treated is a macroadenoma. In embodiments, the pituitary adenoma is an adenoma selected from a corticotroph (including a corticotroph with significant amounts of Crooke's hyalinazation, a corticotroph with little or no Crooke's hyalinization, and a silent corticotroph); a somatotroph; a lactotroph; a thyrotroph; a gonadotroph; and an oncocytoma. In embodiments, the pituitary tumor to be reduced in size is pituitary tumor selected from a nonfunctional pituitary tumor; a growth hormone-secreting tumor; a gonadotropin-secreting tumor (e.g., secreting LH or FSH); or other tumor.

The methods for reducing the size of pituitary tumors comprise administration of relacorilant ((R)-(1-(4-fluorophenyl)-6((1-methyl-1H-pyrazol-4-yl)sulfonyl)-4,4a,5,6,7, 8-hexahydro-1H-pyrazolo[3,4-g]isoquinolin-4a-yl) (4-(trifluoromethyl)pyridin-2-yl)methanone), which has the following structure:

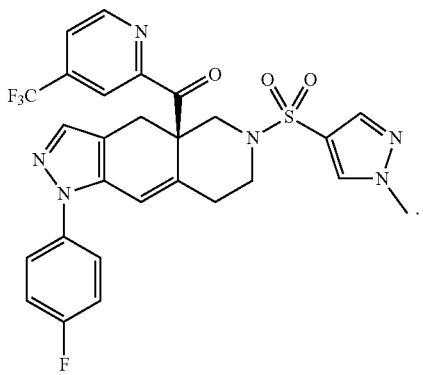 [SMILES: Cn1cc(S(=O)(=O)N2CCC3=Cc4c(cnn4-c4ccc(F)cc4)C[C@]3(C(=O)c3cc(C(F)(F)F)ccn3)C2)cn1]

Relacorilant is also known as CORT125134. Relacorilant is a glucocorticoid receptor modulator (GRM) that does not significantly affect progesterone, mineralocorticoid, androgen, or estrogen receptors (see, e.g., U.S. Pat. Nos. 8,859,774; 9,273,047; 9,707,223; and 9,956,216, the entire contents of all of which patents are hereby incorporated by reference in their entireties). In embodiments, relacorilant is administered orally.

In embodiments, an image (e.g., a magnetic resonance imaging (MRI), positron emission tomography (PET) image, computer assisted tomography (CAT) image, or other image) is made of the pituitary tumor, and then relacorilant is administered. The image of the pituitary tumor may be obtained from imaging at least a portion of the brain of, and nearby anatomical regions of, the patient. In embodiments, such imaging may provide a general, and in embodiments, a precise, localization of the tumor with respect to anatomical landmarks and anatomical regions at or near the pituitary of the patient. For example, such anatomical landmarks and anatomical regions may include, without limitation, the sella turcia, the pituitary stalk, the hypothalamus, a temporal lobe, a brain ventricle, the optic nerve or optic chiasm, the brainstem, the corpus callosum, and other anatomical structures near the pituitary gland or otherwise visible in an image that includes the pituitary. In embodiments, a dimension of the tumor is measured using an image of the pituitary tumor. In embodiments, a first image (e.g., an MRI, PET, CAT, or other image) is made of the pituitary tumor, relacorilant is then administered, and, after a period of time of relacorilant treatment, a second image (e.g., an MRI, PET, CAT, or other image) of the pituitary tumor is made. In embodiments, a first image of the pituitary tumor is made, relacorilant is then administered, and, after a period of time of relacorilant treatment, a second image of the pituitary tumor is made, and then a further treatment is applied to the pituitary tumor. In embodiments, such further treatment is surgical treatment; or radiation treatment; or pharmaceutical or chemotherapeutic treatment; or combinations thereof. The period of time may be, for example, a day, a week, or a month, or several months during which the patient receives relacorilant on a regular basis; such a regular basis may be, for example, daily relacorilant administration. Administration of relacorilant may be oral administration of relacorilant.

Accordingly, in embodiments, Applicant discloses herein new and surprising treatment methods directed to patients suffering from pituitary tumors, the methods comprising administration of relacorilant to a patient suffering from a pituitary tumor effective to reduce the size of the pituitary tumor. Applicant discloses herein, for example, that a few months of relacorilant treatment was effective to reduce the size of pituitary tumors (both macroadenomas) in two Cushing's Disease patients.

These methods are surprising, for example, in view of the finding that there was no regression in any of 17 Cushing's Disease patients with visible tumors treated with mifepristone for 24 weeks (10 of which were macroadenomas). The tumors were imaged using magnetic resonance imaging (MRI); the MRI images were stable in all but one patient, in whom the tumor increased in size with 10 weeks of mifepristone treatment (Fleseriu, et al., *J Clin Endocrin Metab* 97(6):2039-2049 (2012)).

In embodiments, Applicant discloses herein new and surprising treatment methods directed to the tumors of patients suffering from pituitary tumors, which may be, e.g., pituitary adenomas. In embodiments, the treatment methods are directed to patients suffering from non-functional (i.e., non-secreting pituitary tumors). In embodiments, the treatment methods are directed to patients suffering from hormone-secreting pituitary tumors, which may be, e.g., adrenocorticotrophic hormone (ACTH)-secreting pituitary tumors. In embodiments, the treatment methods are directed to patients suffering from hormone-secreting pituitary tumors, which may be, e.g., GH, TSH, PRL, MSH, FSH, LH, or β-lipotropin-secreting pituitary tumors.

The present methods may be applied to patients suffering from a pituitary tumor effective to shrink the pituitary tumor, as a first-line treatment of the tumor; as neo-adjuvant treatment of the tumor (i.e., preceding a subsequent treatment such as radiation, surgical, or other treatment of the tumor (e.g., as preparation for such treatment)); as adjuvant treatment of the tumor (i.e., following surgical, radiation, or other treatment of the pituitary tumor); and in other uses and combinations. The present methods may be applied to patients suffering from a pituitary tumor that is visible using clinical imaging. The present methods may be applied to patients suffering from a pituitary tumor the size of which is measurable using clinical imaging. Pituitary tumors are often treated surgically; such surgical treatment for pituitary tumors may be, e.g., transsphenoidal surgery. In embodiments, the treatment methods are directed to patients suffering from pituitary tumors, who are not candidates for surgery, or who have refused surgery, or who have failed surgery, where the surgery may be transsphenoidal surgery or may be other surgery for treatment of the pituitary tumor. In embodiments, the treatment methods are directed to patients suffering from pituitary tumors, who are candidates for surgery, who have not yet undergone surgery, where the surgery may be transsphenoidal surgery or may be other surgery for treatment of the pituitary tumor. In embodiments, the treatment methods are directed to patients suffering from pituitary tumors, for whom surgery is planned, but who have not yet undergone surgery, in which administration of relacorilant comprises preparation or pre-treatment for surgery, where the surgery may be transsphenoidal surgery or may be other surgery for treatment of the pituitary tumor. In embodiments, the treatment methods are directed to patients suffering from pituitary tumors, which patients have previously undergone surgery for treatment of the pituitary tumors, which treatment was not successful, or was incompletely successful, or following which the tumors have regrown, where the surgery may be transsphenoidal surgery or may be other surgery for treatment of the tumor.

In embodiments, the treatment methods are directed to patients suffering from pituitary tumors, which patients have previously undergone radiation treatment for the pituitary tumors, which treatment was not successful, or was incompletely successful, or following which the tumors have regrown.

Accordingly, Applicant discloses herein methods of treating a visible pituitary tumor comprising administering relacorilant to the patient, effective treat the pituitary tumor, wherein said treatment comprises reducing the size of the pituitary tumor. Applicant discloses herein methods of reducing the size of a pituitary tumor comprising administering relacorilant to the patient, effective to reduce the size of the pituitary tumor; such reduction of the size of the pituitary tumor may be irrespective of the functional status of the pituitary tumor. Applicant discloses herein methods of treatment of a visible pituitary tumor comprising administering relacorilant to the patient, effective to reduce the size of the visible pituitary tumor. Applicant discloses herein methods of treatment of a pituitary tumor comprising administering relacorilant to the patient, effective to reduce hormone secretion from the pituitary tumor. Applicant discloses herein methods of treatment of a pituitary tumor comprising administering relacorilant to the patient, effective to treat the pituitary tumor to reduce ACTH secretion from the pituitary tumor. The methods may include selecting a patient for such treatment, where the patient suffers from such a pituitary tumor; where the patient suffers from a visible pituitary tumor; where the patient suffers from a measurable pituitary tumor. The methods may include selecting a patient for such treatment, where the patient suffers from such a pituitary tumor and suffers from symptoms of Cushing's syndrome; or suffers from excess ACTH levels; or from excess cortisol levels; or from a pituitary tumor that causes symptoms of Cushing's syndrome.

Relacorilant administration may comprise oral administration of relacorilant, and may be to a patient in the fasted, or in the fed, condition. The pituitary tumor may be an adenoma, and may be a hormone-secreting pituitary tumor. The pituitary tumor may be an ACTH-secreting pituitary tumor. The treatment may comprise relacorilant administration prior to pituitary surgery, during pituitary surgery, after pituitary surgery, and combinations thereof (where such pituitary surgery may include, e.g., surgical resection of the tumor). In embodiments, the treatment methods may further comprise radiation, or (for pituitary carcinomas) chemotherapy treatments. Such radiation or chemotherapy treatments may be administered prior to surgery, during surgery, after surgery, or combinations thereof.

The present methods comprising administering relacorilant to patients suffering from pituitary tumors provide new and useful treatments for patients, such as, e.g., Cushing's Disease patients who have, or have had, a pituitary tumor. Such a pituitary tumor may be, e.g., an adenoma in or near the pituitary, and may be a visible tumor, and may be a measurable tumor. The present methods may be useful to reduce the size of pituitary tumors without surgery. The present methods may be useful to prepare a patient with a pituitary tumor for transsphenoidal surgery, and may improve the efficacy of such surgery by shrinking pituitary tumor tissue making it more amenable to surgical resection. The present methods comprising administration of relacorilant may be useful during transsphenoidal surgery. The present methods comprising administration of relacorilant may be useful following transsphenoidal surgery by reducing the size of, slowing or preventing regrowth of, and reducing or preventing proliferation of tumor tissue that remain following transsphenoidal surgery.

Accordingly, the present methods provide further new and useful treatments for patients suffering from pituitary tumors, such as Cushing's Disease patients suffering from a pituitary tumor, by providing alternatives to, and adjuncts to, transsphenoidal surgery or other surgical treatment of a pituitary tumor. These methods provide advantages including providing new treatment alternatives, including alternatives to surgery; providing pre-surgical treatments; improving surgical treatments and outcomes; and providing post-surgical treatments (alone or in combination with e.g., radiation treatment or cancer chemotherapy treatment) that may reduce the need for further surgery. The present methods are believed to provide significant advantages to patients suffering from pituitary tumors by shrinking pituitary tumor tissue before surgery, or during surgery, or both; and by shrinking any pituitary tumor tissue that may remain after surgery effective to prevent, reduce or delay recurrence of Cushing's Disease symptoms after surgery.

In view of the lack of medical (i.e., non-surgical) treatments for pituitary tumors, including the lack of medical treatments for pituitary adenomas, the ability to reduce the size of a pituitary tumor without surgery, and with a short duration of treatment, is surprising and advantageous. Such reduction in size of the pituitary tumor with a short duration of treatment may be effective to reduce hormone secretion from the tumor, which is also surprising and advantageous.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 3A shows a pretreatment pituitary MRI image of the patient suffering from pituitary Cushing's syndrome (this is a further image from the patient of FIG. 2A and FIG. 2B). This image is an anterior-posterior coronal view, and shows the patient's macroadenoma. The left and right cerebral arteries are indicated by arrows.

FIG. 3B shows a subsequent anterior-posterior coronal MRI image, following treatment with relacorilant, obtained after the image of FIG. 3A from the same patient imaged for FIGS. 2A, 2B, and 3A.

FIG. 3C shows a pretreatment MRI image from the patient of FIGS. 2A, 2B, 3A, and 3B, showing the patient's macroadenoma in a coronal lateral view.

FIG. 3D shows a post-treatment MRI image from the patient of FIGS. 2A, 2B, 3A, 3B, and 3C, showing the patient's macroadenoma in a coronal lateral view.

DETAILED DESCRIPTION

A. Introduction

Figure 1A:
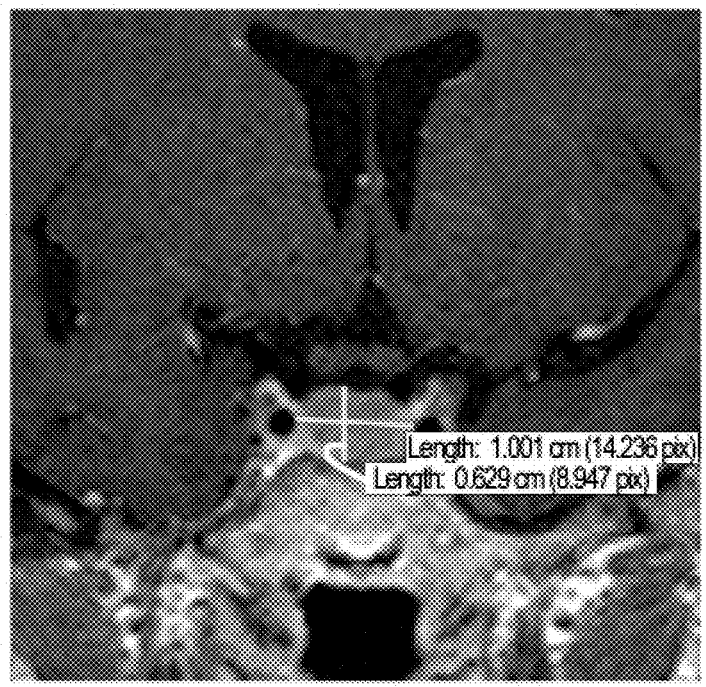
FIG. 1A shows a coronal magnetic resonance imaging (MRI) image from a patient suffering from pituitary Cushing's syndrome without history of pituitary irradiation. (This patient is discussed in Example 1.) The image shows a cross-section of the patient's macroadenoma prior to treatment. The macroadenoma had dimensions of 1.001 centimeters (cm) (14.236 pixels) by 0.629 cm (8.947 pixels) before treatment with relacorilant.

The methods disclosed herein can be used to treat a patient suffering from a pituitary tumor by administering relacorilant effective to reduce the size of the pituitary tumor. In embodiments, the patient suffers from a symptom of Cushing's syndrome, and may suffer from Cushing's Disease. The pituitary tumor may be a visible pituitary tumor (i.e., may be visible by clinical imaging techniques). The pituitary tumor may be a measurable pituitary tumor (i.e., the size, such as at least one dimension, of the pituitary tumor may be able to be measured by clinical imaging or other techniques). The pituitary tumor may be both visible and measurable. In embodiments, the methods include selecting a patient suffering from a pituitary tumor and suffering from symptoms of Cushing's syndrome, and administering relacorilant effective to reduce the size of the pituitary tumor. Imaging techniques may be utilized in selecting the patient for treatment. In embodiments, the tumor may be a non-functional (non-secreting) pituitary tumor; or may be a hormone-secreting pituitary tumor. In embodiments, the tumor may be a pituitary adenoma (e.g., a pituitary macroadenoma). In embodiments, the methods include selecting a patient suffering from a pituitary tumor and having excess adrenocorticotropic hormone (ACTH) levels, and administering relacorilant effective to reduce the size of the pituitary tumor. In embodiments, the methods include selecting a patient suffering from a pituitary tumor and having excess cortisol levels, and administering relacorilant effective to reduce the size of the pituitary tumor. In embodiments, the methods include selecting a patient suffering from a pituitary tumor that causes symptoms of Cushing's syndrome, and administering relacorilant effective to reduce the size of the pituitary tumor. The tumor may be a hormone-secreting neuroendocrine tumor, may be an adenoma, and may be a macroadenoma. In embodiments, the pituitary tumor is a pituitary adenoma, and may be a pituitary macroadenoma. In embodiments, the treatment methods are directed to patients suffering from hormone-secreting pituitary tumors. In embodiments, the hormone-secreting pituitary tumors may secrete a hormone such as, e.g., ACTH, GH, TSH, PRL, MSH, FSH, LH, β-lipotropin, oxytocin, or vasopressin. In embodiments, the treatment methods are directed to patient suffering from a hormone-secreting pituitary tumor which secretes adrenocorticotrophic hormone (ACTH). In embodiments, the methods include selecting a patient suffering from a hormone-secreting pituitary tumor, and administering relacorilant effective to reduce the size of the pituitary tumor and/or to reduce hormone secretion from the tumor.

Novel treatment methods disclosed herein comprise administering relacorilant to the patient suffering from a pituitary tumor, effective to reduce the size of the pituitary tumor. Treatment of patients suffering from a visible pituitary tumor with relacorilant is disclosed herein to be effective to reduce the size of the pituitary tumor. In embodiments, the methods include identifying a patient for whom the present methods are suitable, e.g., by detecting a pituitary tumor, and in embodiments, identifying a patient for whom the present methods are preferable to other methods, whether provided as first line treatment, or in conjunction with other treatments. In embodiments, the methods include selecting a patient for whom the present methods are suitable, e.g., by detecting, classifying, or measuring the size of a pituitary tumor, and in embodiments, selecting a patient for whom the present methods are preferable to other methods, whether provided as first line treatment, or in conjunction with other treatments.

In embodiments, the methods include selecting a patient suffering from a pituitary tumor that is visible, and which may be measurable, using clinical imaging techniques (e.g., MRI, PET, CAT, and other imaging techniques and technologies). In embodiments, the methods include selecting a patient suffering from a pituitary macroadenoma (a pituitary adenoma measuring 10 millimeters (mm) or greater in at least one dimension). In embodiments, the methods include selecting a patient suffering from a pituitary microadenoma (a pituitary adenoma measuring less than 10 mm in all three dimensions). In embodiments, the methods include selecting a patient suffering from a pituitary tumor greater in size than about 5 millimeters (mm) (in a single dimension), or having a cross-sectional area of greater than about 20 $mm^2$, or having a volume estimated to be greater than about 100 $mm^3$. In embodiments, the methods include selecting a patient suffering from a visible pituitary tumor and suffering from symptoms of Cushing's syndrome; or selecting a patient suffering from a visible pituitary tumor and having excess adrenocorticotropic hormone (ACTH) levels (e.g., greater than about 10 pmol/L); or selecting a patient suffering from a visible pituitary tumor and having excess cortisol levels (e.g., greater than about 3 nmol/L or about 4 nmol/L at night, or greater than about 23 nmol/L, or about 27 nmol/L, in the morning); or selecting a patient suffering from a visible pituitary tumor that causes symptoms of Cushing's syndrome; or selecting a patient suffering from a visible pituitary tumor whose results of a dexamethasone suppression test (DST) are less than 1.8 micrograms/deciLiter (mcg/dL); or selecting a patient suffering from a visible pituitary tumor whose late night serum cortisol (LNSC) is greater than 18 nanograms per milliliter (ng/mL) (greater than 50 nanomoles per Liter (nmol/l)); or selecting a patient suffering from a visible pituitary tumor whose urinary free cortisol (UFC) is above the upper normal range (e.g., above the upper normal range for a patient of that sex, or above the upper normal range for the particular assay used to determine UFC); and administering relacorilant effective to reduce the size of the pituitary tumor. In embodiments, the visible pituitary tumor is a measurable pituitary tumor, i.e., the tumor size (in at least one dimension) is measurable using clinical imaging or other techniques.

The pituitary tumor may be a pituitary adenoma (including, e.g., a pituitary macroadenoma or a pituitary microadenoma); treatment of a patient suffering from a pituitary adenoma with relacorilant is disclosed herein to be effective to reduce the size of the pituitary adenoma. In embodiments, the tumor is a non-invasive tumor. In embodiments, the tumor is not metastatic. In embodiments, the tumor is an invasive tumor. In embodiments, the tumor is a metastatic tumor. Administration of relacorilant to a patient suffering from a pituitary adenoma may be effective to reduce hormone secretion from the pituitary adenoma. Administration of relacorilant to a patient suffering from a pituitary tumor may be effective to ameliorate symptoms associated with the pituitary tumor. In embodiments, symptoms associated with the pituitary tumor comprise symptoms of Cushing's syndrome, and may include symptoms of Cushing's Disease. In embodiments, the patient suffers from Cushing's syndrome. In embodiments, the patient suffers from Cushing's Disease. In embodiments, the patient is identified as having such a pituitary tumor, or as suffering from one or more of such symptoms or disorders, and is selected for treatment based on that identification.

In view of the lack of medical (i.e., non-surgical) treatments for pituitary tumors, including the lack of medical treatments for pituitary adenomas, the ability to reduce the size of a pituitary tumor without surgery, and with a short duration of treatment, is surprising and advantageous. Such reduction in size of the pituitary tumor with a short duration of treatment may be effective to reduce hormone secretion from the tumor, which is also surprising and advantageous.

In embodiments, the methods disclosed herein include administering an effective amount of relacorilant, in combination with pituitary tumor targeting treatments (e.g., surgical treatment, radiation treatment, pharmaceutical therapy, chemotherapy, or combinations thereof). In embodiments, such combination treatments are administered to a patient who has received relacorilant treatment prior to surgery. In embodiments, such combination treatments are administered to a patient following surgery to reduce the size of, or to remove, the pituitary tumor.

Accordingly, Applicant discloses herein methods of treatment of a pituitary tumor comprising administering relacorilant to the patient, effective to reduce the size of the pituitary tumor. In embodiments, the methods of treatment of a pituitary tumor in a patient comprise administering relacorilant to the patient, effective to reduce hormone secretion from the pituitary tumor. In embodiments, the methods of treatment of a pituitary tumor comprise administering relacorilant to the patient prior to surgical treatment of the pituitary tumor. In embodiments, such surgical treatment of the pituitary tumor comprises surgical resection of the tumor. Transsphenoidal surgery is often used to perform surgical resection of a pituitary tumor. It will be understood that surgical resection of the tumor may comprise partial resection, and may comprise full resection, of the pituitary tumor. In embodiments, the methods of treatment of a pituitary tumor comprise administering relacorilant to the patient prior to surgical treatment of the pituitary tumor, effective to reduce the size of the pituitary tumor prior to said surgical treatment. In embodiments, the methods of treatment of a pituitary tumor comprise administering relacorilant to the patient following surgical treatment of the pituitary tumor. In embodiments, the methods of treatment of a pituitary tumor comprise administering relacorilant and one or both of radiation treatment and cancer chemotherapy treatment, to the patient following surgical treatment of the pituitary tumor. In embodiments, the methods comprising relacorilant administration following surgical treatment of the pituitary tumor are effective to treat pituitary tumor tissue remaining following said surgical treatment. In embodiments, the methods comprising relacorilant administration following surgical treatment of the pituitary tumor are effective to reduce the size of pituitary tumor tissue remaining following said surgical treatment. In embodiments, the methods comprising relacorilant administration following surgical treatment of the pituitary tumor are effective to reduce the subsequent growth of pituitary tumor tissue remaining following said surgical treatment.

In preferred embodiments, the administration of relacorilant comprises oral administration of relacorilant. In embodiments, the relacorilant is orally administered without food to a fasted patient, i.e., to a patient who has not eaten food for a period of time before administration of relacorilant. In embodiments, the relacorilant is orally administered with food, or within a short period of time after the patient began eating a meal (e.g., within one hour, or within 30 minutes, after beginning a meal). In embodiments, the relacorilant is administered in conjunction with another therapeutic treatment, where "in conjunction" includes simultaneous administration, and includes administration of relacorilant to a patient who has previously, or soon thereafter, receives another therapeutic treatment. Such other therapeutic treatment may be, for example, a pituitary tumor targeting treatment (e.g., surgical treatment, radiation treatment, pharmaceutical therapy, cancer chemotherapy where the tumor is a carcinoma, or combinations thereof).

The present methods provide further new and useful treatments for patients suffering from pituitary tumors, by further providing administration of relacorilant as a post-operative medical treatment in patients following surgery for treatment of a pituitary tumor. Surgical resection or ablation of tumors is not always complete, and some tumor tissue may remain after surgery or may grow back after surgery. The present methods providing post-operative relacorilant administration provides the advantage of preventing, reducing or delaying recurrence of tumor growth after surgery to surgically remove, or surgically reduce the size of, the tumor. Such post-operative relacorilant treatment, alone or in combination with a pituitary tumor targeting treatment (e.g., further surgical treatment, radiation treatment, pharmaceutical therapy, cancer chemotherapy where the tumor is a carcinoma, or combinations thereof), is believed to provide significant advantages to tumor patients suffering from pituitary tumors by shrinking any tumor tissue that may remain after surgery effective to prevent, reduce or delay recurrence tumor growth or symptoms related to tumor presence or growth after surgery.

The present methods of administering relacorilant to patients suffering from, or who have suffered from, pituitary tumors provide new and useful treatments for patients, such as, e.g., Cushing's Disease patients. Patients for whom the relacorilant treatments disclosed herein are useful include Cushing's Disease patients who have a pituitary tumor, and may include Cushing's Disease patients who had a pituitary tumor that was previously treated by surgery, radiation, or other treatment. Such a pituitary tumor may be, e.g., an adenoma in or near the pituitary. According to the present methods, relacorilant may be administered to a patient suffering from a pituitary tumor effective to reduce the size of (shrink) the tumor, or to reduce symptoms of Cushing's Disease by shrinking the tumor, or both. Further according to the present methods, relacorilant may be administered to a patient suffering from a pituitary tumor prior to surgery to remove part or all of that tumor, effective to improve the ease of surgery, or to improve the outcome of the surgery, or to improve the accessibility of the tumor during the surgery, or to increase the fraction of tumor removed by the surgery (all of which are taken as compared to the ease, outcome, accessibility, or fraction expected to be removed, as would be expected by the same surgery performed without prior relacorilant treatment).

The present methods provide new and useful treatments for patients suffering from pituitary tumors, such as Cushing's Disease patients suffering from a pituitary tumor such as, e.g., a macroadenoma. Administration of relacorilant to reduce the size of pituitary tumors provides a new treatment for such tumors, which may serve as an alternative to surgical treatment, or may be used with surgical or other pituitary targeting treatment. For example, administration of relacorilant to a patient suffering from a pituitary tumor may be the first, and may be the sole, treatment administered to the patient to shrink the tumor. Thus, as an alternative to surgery, relacorilant administration alone may be used to treat patients suffering from pituitary tumors effective to reduce the size of the tumors. As an adjunct to surgical treatment of pituitary tumors, relacorilant may be administered at any time or times before, during, and after surgery (e.g., transsphenoidal surgery to resect a pituitary tumor). Thus, in embodiments, the present methods may serve as first line treatments. In embodiments, the present methods may serve as neoadjuvant treatments; and in embodiments, may serve as adjuvant treatments. In embodiments, such neoadjuvant and adjuvant treatments may be combined with surgical treatment of the pituitary tumor. In embodiments, such neoadjuvant and adjuvant treatments may be combined with radiation treatment of the pituitary tumor. In embodiments, such neoadjuvant and adjuvant treatments may be combined with medical (e.g., pharmaceutical) treatment of the pituitary tumor. In embodiments, such neoadjuvant and adjuvant treatments may be combined with cancer chemotherapy treatment of the pituitary tumor (e.g., where the pituitary tumor is a carcinoma).

The present methods provide administration of relacorilant as a pre-operative medical treatment in patients with Cushing's Disease. Such pre-operative treatment to shrink pituitary tumors provides the advantage of aiding subsequent surgery to surgically remove, or surgically reduce the size of, the tumor. Such pre-operative relacorilant treatment to shrink pituitary tumors is believed to provide significant advantage to patients suffering from pituitary tumors by shrinking the tumor prior to surgery effective to reduce or eliminate tumor invasion of bone or other cranial regions prior to surgery, and thereby improve the amount of tumor amenable to surgical resection. Administration of relacorilant during surgery may also aid treatment during and after surgery.

The present methods provide further new and useful treatments for patients suffering from pituitary tumors, such as Cushing's Disease patients suffering from a pituitary tumor such as, e.g., a macroadenoma, by further providing administration of relacorilant as a post-operative medical treatment in patients with Cushing's Disease. Surgical ablation of pituitary tumors is not always complete, and some tumor tissue may remain after surgery or may grow back after surgery. The present methods providing post-operative relacorilant administration provides the advantage of preventing, reducing or delaying recurrence of Cushing's Disease symptoms after surgery to surgically remove, or surgically reduce the size of, the tumor. Such post-operative relacorilant treatment, alone or in combination with pituitary targeting treatments (e.g., surgical treatment, radiation treatment, pharmaceutical therapy, cancer chemotherapy where the tumor is a carcinoma, or combinations thereof)), and is believed to provide significant advantages to pituitary tumor patients following surgery by shrinking any tumor tissue that may remain after surgery effective to prevent, reduce or delay recurrence of Cushing's Disease symptoms after surgery.

Applicant discloses herein the use of relacorilant to reduce the size of a pituitary tumor in a patient suffering from a pituitary tumor. The pituitary tumor may be a visible pituitary tumor (i.e., may be visible by clinical imaging techniques). The pituitary tumor may be a measurable pituitary tumor (i.e., the size, such as at least one dimension, of the pituitary tumor may be able to be measured by clinical imaging or other techniques). The pituitary tumor may be both visible and measurable. Imaging techniques may be utilized in identifying and in selecting the patient for treatment. In embodiments, the tumor may be a non-functional (non-secreting) pituitary tumor; or may be a hormone-secreting pituitary tumor. In embodiments, the tumor may be a pituitary adenoma (e.g., a pituitary macroadenoma).

In embodiments, the use of relacorilant is directed to patients suffering from hormone-secreting pituitary tumors. Applicant discloses herein the use of relacorilant to reduce hormone secretion from a hormone-secreting pituitary tumor. The tumor may be a hormone-secreting neuroendocrine tumor, may be an adenoma, and may be a macroadenoma. In embodiments, the pituitary tumor is a pituitary adenoma, and may be a pituitary macroadenoma. In embodiments, the pituitary tumor may secrete adrenocorticotropic hormone (ACTH) levels, and cause excess ACTH in the patient. administering relacorilant effective to reduce the size of the pituitary tumor. In embodiments, the use of relacorilant to reduce ACTH secretion from a pituitary tumor may treat excess cortisol activity in the patient. In embodiments, the use of relacorilant in treating a patient suffering from a pituitary tumor may reduce symptoms of Cushing's syndrome, and may reduce symptoms of Cushing's Disease. In embodiments, the hormone-secreting pituitary tumors may secrete a hormone such as, e.g., ACTH, GH, TSH, PRL, MSH, FSH, LH, β-lipotropin, oxytocin, or vasopressin. In embodiments, the use of relacorilant is effective to reduce the size of the pituitary tumor and to reduce hormone secretion from the tumor.

B. Definitions

As used herein, the term "Adrenocorticotrophic Hormone" (ACTH) refers to the peptide hormone produced by the anterior pituitary gland that stimulates the adrenal cortex to secrete glucocorticoid hormones, which help cells synthesize glucose, catabolize proteins, mobilize free fatty acids and inhibit inflammation in allergic responses. One such glucocorticoid hormone is cortisol, which regulates metabolism of carbohydrate, fat, and protein metabolism.

As used herein, the term "Cushing's syndrome" refers to an array of symptoms caused by excess cortisol. Cushing's syndrome includes endogenous Cushing's syndrome and ectopic Cushing's syndrome. Such symptoms include, for example, elevated blood pressure, elevated blood glucose, increased weight (typically in the mid-section, and in the face causing a characteristic "moon-face"), immune suppression, thin skin, acne, depression, hirsutism, and other symptoms. Cushing's syndrome patients typically suffer from one or more of high blood sugar, high blood pressure, weight gain (including a characteristic "hump" on the neck or back), hirsuteness, depression, and other symptoms.

As used herein, a "patient suffering from Cushing's syndrome" refers to any patient suffering from Cushing's syndrome, including endogenous Cushing's syndrome; Cushing's Disease; or a condition associated with Cushing's syndrome. A condition associated with Cushing's syndrome may be, without limitation, a condition associated with endogenous Cushing's syndrome; hyperglycemia secondary to hypercortisolism; a condition of hypercortisolism in an endogenous Cushing's syndrome patient, said patient having type 2 diabetes mellitus or glucose intolerance; a condition of hyperglycemia secondary to hypercortisolism in an endogenous Cushing's syndrome patient, and having type 2 diabetes mellitus or glucose intolerance; and other conditions associated with Cushing's syndrome.

As used herein, the term "Cushing's Disease" refers to pituitary-dependent Cushing's syndrome, e.g., excess cortisol caused by pituitary abnormality (typically a pituitary tumor). Cushing's Disease is thus a disease that is a particular type of Cushing's syndrome. The term Cushing's syndrome thus includes reference to Cushing's Disease.

As used herein, the term "tumor" refers to an abnormal growth of tissue that results from excessive cell division. A tumor may be a benign (non-cancerous) tumor, such as, e.g., an adenoma. A benign tumor typically does not metastasize. A tumor may be a carcinoma (a malignant (cancerous) tumor). A tumor may be non-invasive (i.e., may grow in place but not grow into tissues other than the tissue in which it originated; may be termed a "carcinoma in situ"). A tumor may be non-metastatic (not spread to bodily sites other than the site in which it originated). A tumor may be invasive (grow into tissues surrounding the tissue in which the tumor originated). A tumor, e.g., a malignant tumor, may metastasize (spread to bodily sites other than, and which may be distant from, the site in which the tumor originated). A tumor may metastasize.

Pituitary tumors may be adenomas, or carcinomas; may be non-functional (i.e., non-secreting) tumors; may be secreting tumors (including hormone-secreting adenomas (e.g., ACTH-secreting adenomas); may neuroendocrine tumors, or other tumors. Adenomas may be, e.g., macroadenomas (having a dimension of 10 mm or greater in at least one direction), and may be microadenomas (having no dimension of 10 mm or greater). Although rare, a pituitary tumor may be a carcinoma, and, in rarer instances, may be a metastasis of a tumor that originated in a different location.

As used herein, the term "hormone-secreting tumor" refers to a tumor, such as an adenoma or a neuroendocrine tumor, that secretes a hormone. Secretion includes release (of the hormone) into the blood, or into lymph, or into surrounding tissue or interstitial fluid. For example, a hormone-secreting pituitary tumor may secrete ACTH. It will be understood that a hormone-secreting tumor may secrete more than one type of hormone. It will be understood that a hormone-secreting tumor may secrete inactive forms of such hormones. Other hormones secreted by the pituitary, and which may be secreted by hormone-secreting pituitary tumors, include growth hormone (GH), prolactin (PRL), thyroid stimulating hormone (TSH), follicle stimulating hormone (FSH), luteinizing hormone (LH), melanocyte stimulating hormone (MSH), β-lipotropin, oxytocin, and vasopressin.

As used herein, the terms "classifying", "to classify", "classification", and the like refer to determining one or more characteristics of a pituitary tumor and using that determination to place the pituitary tumor into its proper classification. Such a classification may include, for example, one or more of adenoma (including either macroadenoma or microadenoma, and which may further be classified as a corticotroph, somatotroph, lactotroph, or gonadotroph), neuroendocrine, non-functional, hormone-secreting, benign, non-invasive, non-metastatic, malignant, invasive, metastatic, and others.

As used herein, the terms "identifying", "to identify", "identification" and the like refer to determining whether or not a patient suffering from a pituitary tumor, or whether or not the pituitary tumor in a patient, is suitable for treatment to reduce the size of the tumor by administration of relacorilant. A visible pituitary tumor, and a patient having a visible pituitary tumor, is a tumor suitable for treatment to reduce the size of the tumor by administration of relacorilant. A measurable pituitary tumor, and a patient having a measurable pituitary tumor, is a tumor suitable for treatment to reduce the size of the tumor by administration of relacorilant. A measurable tumor suitable for treatment to reduce the size of the tumor by administration of relacorilant may be a macroadenoma, and may be a microadenoma visible by imaging. A microadenoma greater in size than about 9 millimeters (mm) (in a single dimension), or greater in size than 8 mm, or 7 mm, or 6 mm, or 5 mm, or 4 mm, or 3 mm, or 2 mm, or 1 mm, or less than 1 mm but still visible with imaging, may be identified as a tumor suitable for treatment to reduce the size of the tumor by relacorilant administration. A pituitary tumor having a cross-sectional area of greater than about 5 square millimeters ($mm^2$), or about 10 $mm^2$, or about 20 $mm^2$, or about 30 $mm^2$, or about 40 $mm^2$, or about 50 $mm^2$, or about 75 $mm^2$, or about 100 $mm^2$, or greater, may be identified as a tumor suitable for treatment to reduce the size of the tumor by relacorilant administration. A pituitary tumor having a volume estimated to be greater than about 5 cubic millimeters ($mm^3$), or about 10 $mm^3$, or about 20 $mm^3$, or about 30 $mm^3$, or about 40 $mm^3$, or about 50 $mm^3$, or about 75 $mm^3$, or about 100 $mm^3$, or about 150 $mm^3$, or about 200 $mm^3$, or greater, may be identified as a tumor suitable for treatment to reduce the size of the tumor by relacorilant administration. Further criteria which may be used to identify a patient suffering from a visible pituitary tumor suitable for treatment to reduce the size of the tumor by relacorilant administration include excess ACTH levels (e.g., greater than about 10 pmol/L); excess cortisol levels (e.g., greater than about 3 nmol/L or about 4 nmol/L at night, or greater than about 23 nmol/L, or about 27 nmol/L, in the morning); symptoms of Cushing's syndrome in the patient; a dexamethasone suppression test (DST) result less than 1.8 micrograms/deciLiter (mcg/dL); late night serum cortisol (LNSC) greater than 18 nanograms per milliliter (ng/mL) (greater than 50 nanomoles per Liter (nmol/1)); and UFC above the upper normal range. Patients with visible tumors and one or more of such characteristics may be identified as suitable for relacorilant administration to reduce the size of the pituitary tumor. Such a patient may be selected for treatment according to the methods disclosed herein.

As used herein, the phrases "reduce in size", "reducing in size", "reduction in size", and the like refer to a lessening in the size of the object or structure to which it refers (e.g., a tumor). A reduction in size of the object or structure may be a reduction in a dimension, or in an area, or in a volume, where the size of the object or structure is first measured with respect to such a dimension, or area, or volume, and a second measurement of that dimension, area, or volume that is made later (e.g., following a treatment such as relacorilant administration) is determined to be less than the first measurement.

As used herein, the term "patient" refers to a human that is or will be receiving, or has received, medical care for a disease or condition.

As used herein, the term "imaging" refers to any method of providing a representation of the anatomy of a patient, or a portion of the anatomy a patient. Such a representation is an "image" and may be provided on a screen, a print-out, a photograph, or otherwise made available for viewing, examination, and use. Imaging techniques include, without limitation, magnetic resonance imaging (MRI); computer-assisted tomography (CAT) imaging; positron-emission tomography (PET) imaging; X-ray imaging; and other forms and techniques of imaging.

As used herein, the term "visible" as in, for example, the phrase "visible tumor", refers to an object, such as a tumor, which may be seen or detected by a person or automated technique by use of imaging. For example, where a patient has been subjected to imaging, and an image of the brain and anatomical regions including the pituitary of the patient has been made, a tumor that is observable or detectable by a clinician, radiologist, MRI technician, or other person examining the output of the imaging technique (e.g., the MRI scan), or that is identifiable by automated or computer-implemented image analysis techniques, is a "visible tumor".

As used herein, the term "measurable" as in, for example, the phrase "measurable tumor", refers to an object, such as a tumor, which may be examined and quantified by a person or automated technique by use of imaging. For example, where a patient has been subjected to imaging, and an image of the brain and anatomical regions including the pituitary of the patient has been made, a tumor whose size (whether length (a single dimension), area (i.e., cross-sectional area, a two-dimensional measurement), or volume (a three-dimensional measurement)) may be measured or estimated by a clinician, radiologist, MRI technician, or other person examining the output of the imaging technique (e.g., the MRI scan) is a "measurable tumor". It will be understood that any measurement, including measurements of the size of a pituitary tumor, is made with respect to the normal and accepted tolerance, precision, and accuracy of imaging or other technique used to obtain that measurement.

As used herein, the terms "localize", "localization", and "localizable" as in, for example, the phrase "localize a tumor", refers to the determination of the position of the tumor within the patient. Such localization may localize a pituitary tumor with respect to anatomical landmarks and anatomical regions at or near the pituitary of the patient, such as, e.g., the sella turcia, the pituitary stalk, the hypothalamus, a temporal lobe, a brain ventricle, the optic nerve or optic chiasm, the brainstem, the corpus callosum, and other anatomical structures near the pituitary gland or otherwise visible in an image that includes the pituitary. Localization of a tumor may be aided by, and may be performed using, imaging. Such localization may be general, or may be specific, a precise location of a pituitary tumor within the patient's skull may be obtained using imaging techniques (where precise is understood to be with respect to the normal and accepted tolerance, precision, and accuracy of the techniques used).

As used herein, the terms "administer," "administering," "administered" or "administration" refer to providing a compound or a composition (e.g., one described herein), to a subject or patient. For example, a compound or composition may be administered orally to a patient.

As used herein, the term "effective amount" or "therapeutic amount" refers to an amount of a pharmacological agent effective to treat, eliminate, or mitigate at least one symptom of the disease being treated. In some cases, "therapeutically effective amount" or "effective amount" can refer to an amount of a functional agent or of a pharmaceutical composition useful for exhibiting a detectable therapeutic or inhibitory effect. The effect can be detected by any assay method known in the art.

As used herein, the term "period of time" refers to an interval between two events; for example, the period of time referred to in the phrase "has not eaten food for a period of time before administration of relacorilant" is that time interval between the end of the last meal eaten by a subject (first event) and the time of administration of relacorilant (second event). A "short period of time" referring to a meal may be, e.g., 15 minutes, or 30 minutes, or one hour. A period of time may also refer to the period of time during which a patient receives a treatment, such as, e.g., daily administration of relacorilant. Periods of time referring to administration of relacorilant may refer to days, or weeks, or months, or years of such administration. Such administration may be daily administration of relacorilant during that period of time, or may be administration every other day, or every third day, or every fourth day, or every week, or other schedule of administration.

As used herein, the term "duration" as applied to, e.g., the duration of treatment of a patient, refers to that period of time during which the patient receives treatment. Such treatment is typically repetitive treatment such as daily administration of a drug (e.g., relacorilant), or administration of a drug every other day, or by some other schedule of administration. A duration of administration may be a few days; a week, or a few weeks; a month, or a few months, or more than 6 months; or a year, or two years, or more. A short duration of treatment may be one year or less; or eleven months or less; or ten months or less; or nine months or less; or six months or less; or three months or less. A short duration of treatment may be with regard to alternative treatments; for example, where an alternative treatment was applied for one year, or for two years, a duration of treatment of less than one year is a short duration of treatment.

As used herein, the term "combination therapy" refers to the administration of at least two pharmaceutical agents or medical treatments (or at least a pharmacological agent and a medical treatment) to a subject to treat a disease. The at least two agents or treatments of a combination therapy are administered in conjunction with each other. The at least two agents or treatments may be administered simultaneously, or sequentially in any order during the entire or portions of the treatment period. The at least two agents or treatments may be administered following the same or different dosing regimens. In some cases, one agent or treatment is administered following a scheduled regimen while the other agent or treatment is administered intermittently. In some cases, both agents or treatments are administered intermittently. In some embodiments, a pharmaceutical agent, e.g., relacorilant, may be administered daily, and the other pharmaceutical agent or treatment, e.g., radiation therapy or a chemotherapeutic agent, may be administered once, or at intervals, e.g., every two, three, or four days, or twice in a month, or other interval or period.

As used herein, the term "composition" is intended to encompass a product comprising ingredients such as the said compound, its tautomeric form, its derivatives, its analogues, its polymorphs, its deuterated species, its pharmaceutically acceptable metabolites, mixtures of isomers, its pharmaceutically acceptable solvates and pharmaceutically acceptable compositions in specified amounts, as well as any product which results, directly or indirectly, from combination of the specified ingredients in the specified amounts. Such a term in relation to a pharmaceutical composition is intended to encompass a product comprising the active ingredient (s), and the inert ingredient (s) that make up the carrier, as well as any product which results, directly or indirectly, in combination, complexation or aggregation of any two or more of the ingredients, or from dissociation of one or more of the ingredients, or from other types of reactions or interactions of one or more of the ingredients. Accordingly, the pharmaceutical compositions of the present invention are meant to encompass any composition made by admixing compounds of the present invention and their pharmaceutically acceptable carriers.

As used herein, the term "pharmaceutically acceptable carrier" is intended to include any and all solvents, dispersion media, coatings, antibacterial and antifungal agents, antioxidant agents, isotonic and absorption delaying agents, and the like, compatible with pharmaceutical administration. Non-limiting examples of pharmaceutically-acceptable excipients include water, NaCl, normal saline solutions, lactated Ringer's, normal sucrose, normal glucose, binders, fillers, disintegrants, encapsulating agents, plasticizers, lubricants, coatings, sweeteners, flavors and colors, and the like. One of ordinary skill in the art will recognize that other pharmaceutical excipients are useful in the present invention. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

As used herein, the term "glucocorticoid receptor" ("GR") refers to the type II GR, a family of intracellular receptors which specifically bind to cortisol and/or cortisol analogs such as dexamethasone (See, e.g., Turner & Muller, J. Mol. Endocrinol. Oct. 1, 2005, 35:283-292). The glucocorticoid receptor is also referred to as the cortisol receptor. The term includes isoforms of GR, recombinant GR and mutated GR.

The term "glucocorticoid receptor modulator" (GRM) refers to any compound which modulates any biological response associated with the binding of GR to an agonist. For example, a GRM that acts as an agonist, such as dexamethasone, increases the activity of tyrosine aminotransferase (TAT) in HepG2 cells (a human liver hepatocellular carcinoma cell line; ECACC, UK). A GRM that acts as an antagonist, such as mifepristone, decreases the activity of tyrosine aminotransferase (TAT) in HepG2 cells. TAT activity can be measured as outlined in the literature by A. Ali et al., J. Med. Chem., 2004, 47, 2441-2452.

As used herein, the term "selective glucocorticoid receptor modulator" (SGRM) refers to any selective compound which modulates any biological response associated with the binding of a GR to an agonist. By "selective," the compound preferentially binds to the GR rather than other nuclear receptors, such as the progesterone receptor (PR), the mineralocorticoid receptor (MR) or the androgen receptor (AR). It is preferred that the SGRM bind GR with an affinity that is 10× greater ($1/10^{th}$ the $K_d$ value) than its affinity to the MR, AR, or PR, both the MR and PR, both the MR and AR, both the AR and PR, or to the MR, AR, and PR. In a more preferred embodiment, the SGRM binds GR with an affinity that is 100× greater ($1/100^{th}$ the $K_d$ value) than its affinity to the MR, AR, or PR, both the MR and PR, both the MR and AR, both the AR and PR, or to the MR, AR, and PR. In another embodiment, the SGRM binds GR with an affinity that is 1000× greater ($1/1000^{th}$ the $K_d$ value) than its affinity to the MR, AR, or PR, both the MR and PR, both the MR and AR, both the AR and PR, or to the MR, AR, and PR. Relacorilant is a SGRM.

TREATMENT METHODS

Generally, treatment of a pituitary tumor can be provided by administering an effective amount of relacorilant. As disclosed herein, the size of a pituitary tumor may be reduced by administration of relacorilant. In embodiments, treatment of a patient who has received surgery for treatment of a pituitary tumor can be provided by administering an effective amount of relacorilant and one or both of radiation treatment and cancer chemotherapeutic treatment.

In some cases, the effective amount of relacorilant is a daily dose of between 1 and 100 mg/kg/day. In embodiments, the daily dose of relacorilant is 1, 2, 4, 6, 8, 10, 12, 14, 16, 18, 20, 30, 40, 50 60, 70, 80, 90 or 100 mg/kg/day. In embodiments, the daily dose of relacorilant is 10, 20, 40, 60, 80, 100, 125, 150, 200, 250, 300, 350, 400, 450, 500, or 750 mg/day. In embodiments, relacorilant is administrated for at least 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, or 80 weeks.

Relacorilant (also known as is CORT 125134) is (R)-(1-(4-fluorophenyl)-6-((1-methyl-1H-pyrazol-4-yl)sulfonyl)-4, 4a,5,6,7,8-hexahydro-1H-pyrazolo[3,4-g]isoquinolin-4a-yl) (4-(trifluoromethyl)pyridin-2-yl)methanone, which has the following structure:

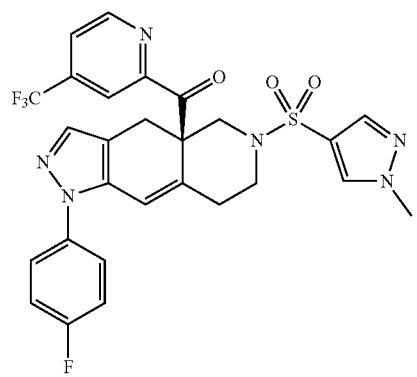 [SMILES: Cn1cc(S(=O)(=O)N2CCC3=Cc4c(cnn4-c4ccc(F)cc4)C[C@]3(C(=O)c3cc(C(F)(F)F)ccn3)C2)cn1]

(see Example 18, U.S. Pat. No. 8,859,774, hereby incorporated by reference in its entirety).

PHARMACEUTICAL COMPOSITIONS AND ADMINISTRATION

In embodiments, the present invention provides a pharmaceutical composition containing relacorilant for treating pituitary tumors, the pharmaceutical composition including a pharmaceutically acceptable excipient and relacorilant.

Relacorilant for shrinking pituitary tumors can be prepared and administered in a wide variety of oral, parenteral and topical dosage forms. Pharmaceutical compositions and dosage forms containing relacorilant are disclosed in U.S. Pat. No. 8,859,774, the entire contents of which is hereby incorporated by reference in its entirety. Oral preparations of relacorilant may include tablets, pills, powder, dragees, capsules, liquids, lozenges, gels, syrups, slurries, suspensions, etc., suitable for ingestion by the patient. Relacorilant may be administered by injection, that is, intravenously, intramuscularly, intracutaneously, subcutaneously, intraduodenally, or intraperitoneally, or by any other suitable means or routes of administration. Any and all of such pharmaceutical compositions and dosage forms containing relacorilant disclosed in U.S. Pat. No. 8,859,774 may be suitable for use in shrinking pituitary tumors.

The pharmaceutical preparation for shrinking pituitary tumors contains relacorilant and is preferably in unit dosage form. In such form the preparation is subdivided into unit doses containing appropriate quantities of relacorilant, the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of relacorilant in a unit dose preparation may be varied or adjusted from 0.1 mg to 10000 mg, more typically 1.0 mg to 6000 mg, most typically 50 mg to 500 mg. Suitable dosages also include about 1 mg, 5, 10, 20, 30, 40, 50, 60, 70, 80, 90, 100, 125, 150, 200, 250, 300, 350, 400, 450, 500, 600, 700, 750, 800, 900, 1000, 1100, 1200, 1300, 1400, 1500, 1600, 1700, 1800, 1900, or 2000 mg. In embodiments, relacorilant may be administered to a patient in single unit doses of 20 milligrams (mg); 30 mg; 40 mg; 50 mg; 75 mg; 100 mg; 125 mg; 150 mg; 175 mg; 200 mg; 250 mg; 300 mg; 350 mg; 400 mg; 450 mg; 500 mg; 600 mg; 700 mg; 800 mg; 900 mg; or 1000 mg. The composition can, if desired, also contain other compatible therapeutic agents.

Single or multiple administrations of formulations can be administered depending on the dosage and frequency as required and tolerated by the patient. The formulations should provide a sufficient quantity of active agent to effectively treat the disease state. Relacorilant may be orally administered, either with food, or without food. Thus, in one embodiment, the pharmaceutical formulation for oral administration of relacorilant provides a daily amount of between about 0.01 to about 150 mg per kilogram of body weight per day (mg/kg/day). In some embodiments, the daily amount is from about 0.1 to 100 mg/kg/day. In embodiments, the daily amount is from about 0.1 mg/kg/day to about 20 mg/kg/day. In embodiments, the daily amount is from about 0.5 mg/kg/day to about 15 mg/kg/day. In embodiments, the daily amount is from about 0.75 mg/kg/day to about 10 mg/kg/day. In embodiments, the daily amount is from about 1 mg/kg/day to about 8 mg/kg/day. Lower dosages can be used, particularly when the drug is administered to an anatomically secluded site, in contrast to administration orally, into the blood stream, into a body cavity or into a lumen of an organ. Substantially higher dosages can be used in topical administration. Actual methods for preparing parenterally administrable formulations will be known or apparent to those skilled in the art and are described in more detail in such publications as *Remington: The Science and Practice of Pharmacy,* 22$^{nd}$ Edition, Pharmaceutical Press, Philadelphia, Pa., 2013. See also Nieman, In "Receptor Mediated Antisteroid Action," Agarwal, et al., eds., De Gruyter, N.Y. (1987).

The duration of relacorilant treatment to reduce the size of a pituitary tumor, reduce hormone secretion from a pituitary tumor, or otherwise treat the tumor or ameliorate the symptoms due to the tumor can vary according to the severity of the condition in a subject and the subject's response to relacorilant. In embodiments, relacorilant is administered daily, and may be orally administered daily. In embodiments, relacorilant may be administered daily for one week; or for two weeks; or for three weeks; or for one month; or for two months; or for three months; or for four months; or for five months; or for six months; or for nine months; or for one year. In some embodiments, relacorilant can be administered for a period of about 1 week to 104 weeks (2 years), more typically about 6 weeks to 80 weeks, most typically about 9 to 60 weeks. Suitable periods of relacorilant administration for shrinking pituitary tumors also include 5 to 9 weeks, 5 to 16 weeks, 9 to 16 weeks, 16 to 24 weeks, 16 to 32 weeks, 24 to 32 weeks, 24 to 48 weeks, 32 to 48 weeks, 32 to 52 weeks, 48 to 52 weeks, 48 to 64 weeks, 52 to 64 weeks, 52 to 72 weeks, 64 to 72 weeks, 64 to 80 weeks, 72 to 80 weeks, 72 to 88 weeks, 80 to 88 weeks, 80 to 96 weeks, 88 to 96 weeks, and 96 to 104 weeks. Suitable periods of administration also include 5, 6, 7, 8, 9, 10, 11, 12, 13, 14, 15, 16, 17, 18, 19, 20, 24, 25, 30, 32, 35, 40, 45, 48 50, 52, 55, 60, 64, 65, 68, 70, 72, 75, 80, 85, 88 90, 95, 96, 100, and 104 weeks. In embodiments, relacorilant for use in shrinking a pituitary tumor is administrated for at least 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, or 80 weeks. Treatment with relacorilant in accordance with the invention may last for as long as two years or even longer.

In some embodiments, administration of relacorilant is not continuous and can be stopped for one or more periods of time, followed by one or more periods of time where relacorilant administration resumes. Suitable periods where relacorilant administration stops include 5 to 9 weeks, 5 to 16 weeks, 9 to 16 weeks, 16 to 24 weeks, 16 to 32 weeks, 24 to 32 weeks, 24 to 48 weeks, 32 to 48 weeks, 32 to 52 weeks, 48 to 52 weeks, 48 to 64 weeks, 52 to 64 weeks, 52 to 72 weeks, 64 to 72 weeks, 64 to 80 weeks, 72 to 80 weeks, 72 to 88 weeks, 80 to 88 weeks, 80 to 96 weeks, 88 to 96 weeks, and 96 to 100 weeks. Suitable periods where relacorilant administration stops also include 5, 6, 7, 8, 9, 10, 11, 12, 13, 14, 15, 16, 17, 18, 19, 20, 24, 25, 30, 32, 35, 40, 45, 48 50, 52, 55, 60, 64, 65, 68, 70, 72, 75, 80, 85, 88 90, 95, 96, and 100 weeks.

The dosage regimen also takes into consideration pharmacokinetics parameters well known in the art, i.e., the rate of absorption, bioavailability, metabolism, clearance, and the like (see, e.g., Hidalgo-Aragones (1996) *J Steroid Biochem. Mol. Biol.* 58:611-617; Groning (1996) *Pharmazie* 51:337-341; Fotherby (1996) *Contraception* 54:59-69; Johnson (1995) *J. Pharm. Sci.* 84:1144-1146; Rohatagi (1995) *Pharmazie* 50:610-613; Brophy (1983) *Eur. J. Clin. Pharmacol.* 24:103-108; and *Remington: The Science and Practice of Pharmacy,* 22n$^d$ Edition, Pharmaceutical Press, Philadelphia, Pa., 2013). In embodiments, the clinician treating the patient may determine the dosage regimen for each individual patient.

Relacorilant for shrinking a pituitary tumor may be used in combination with other active agents or with adjunctive agents that may contribute to the efficacy of relacorilant.

In some embodiments, co-administration includes administering relacorilant within 0.5, 1, 2, 4, 6, 8, 10, 12, 16, 20, or 24 hours of a second agent. Co-administration includes administering two agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the agents may be linked or conjugated to one another.

After a pharmaceutical composition including relacorilant has been formulated in an acceptable carrier, it can be placed in an appropriate container and labeled for treatment of an indicated condition. For relacorilant administration for shrinking a pituitary tumor, such labeling would include, e.g., instructions concerning the amount, frequency and method of relacorilant administration.

Administration of relacorilant for shrinking a pituitary tumor can be combined with other means of treatment such as surgery, radiation, cancer chemotherapy for carcinomas, targeted therapy, immunotherapy, use of growth factor inhibitors, or administration of anti-angiogenesis factors. In embodiments, a patient treated with relacorilant to shrink a pituitary tumor prior to surgery for reduction or removal of the tumor may further receive relacorilant treatment following surgery, and such relacorilant treatment following surgery may be accompanied by other means of treatment such as radiation, cancer chemotherapy for carcinomas, targeted therapy, immunotherapy, use of growth factor inhibitors, or administration of anti-angiogenesis factors. Cancer chemotherapy for carcinomas may include, for example, antimicrotubule agents (e.g., taxanes and vinca alkaloids), topoisomerase inhibitors and antimetabolites (e.g., nucleoside analogs acting as such, for example, Gemcitabine), mitotic inhibitors, alkylating agents, antimetabolites, anti-tumor antibiotics, mitotic inhibitors, anthracyclines, intercalating agents, agents capable of interfering with a signal transduction pathway, agents that promote apoptosis, proteosome inhibitors, and the like. For example, pharmaceutical and other medical therapy for pituitary tumors (including cancer chemotherapy for carcinomas) may include administration of one or more of somatostatin analogues, dopamine agonists, epidermal growth factor receptor (EGFR) antagonists (e.g., anti-EGFR agents such as anti-EGFR antibodies), temozolamide, lomustine (which may be used with 5-Fluorouracil (5FU)), methotrexate (which may be used with 5FU), cisplatin, tamoxifen, carboplatin, cyclophosphamide, doxorubicin, vincristin, bleomycin, seliciclib, etoposide, ubiquitin carboxyl-terminal hydrolase 8 (USP8) inhibitors, chloroquine, peptide receptor radionuclide therapy (PPRT), and combinations thereof. PPRT, also termed radioisotope therapy, is a form of radiation treatment that is administered as a pharmaceutical or medical treatment by injection. For example, where the PPRT includes radiolabeled somatostatin receptor ligand (such as octreotide), the PPRT is a targeted radiation treatment directed to the pituitary, which expresses (or can be treated to express) somatostatin receptors.

The relacorilant administration disclosed herein can reduce tumor size and confer beneficial clinical outcomes to patients having a pituitary tumor. Methods for measuring the size of a pituitary tumor are well-known to skilled artisans in the field. For example, magnetic resonance imaging (MRI) and other imaging methods may be used to detect tumor shrinkage. Other methods for determining the effect of cancer therapy on tumor size are also known in the art, e.g., as described in the Response Evaluation Criteria in Solid Tumors ("RECIST") guidelines, discussed, for example, in Chalian et al., *Radiographics* 31(7):2093-2105 (2011), and available at "protocolDevelopment/docs/recist_guideline.pdf" of the website "ctep.cancer.gov".

Measuring tumor size is typically achieved by imaging-based techniques, including magnetic resonance imaging (MRI), computed tomography (CT), positron-emission tomography (PET) and other techniques. For example, Mill, CT, and PET scans can provide accurate and reliable anatomic information not only about tumor shrinkage or growth but also progression of disease by identifying either growth in existing lesions or the development of new lesions or tumor metastasis. Tumor size, including a reduction in tumor size, may be determined by measuring a linear dimension of a tumor (measuring may be accomplished, for example, by counting pixels on a digital image, by measuring a distance on a printed image or from an image projected onto a screen); by measuring two different linear dimensions of a tumor; by measuring three, or more, different linear dimensions of a tumor; by calculating (or estimating, based on measurements) a cross-sectional area of a tumor; by calculating (or estimating, based on measurements) a volume of a tumor; or by other means known in the art.

In embodiments, a reduction of tumor size can be assessed by functional and metabolic imaging techniques. These techniques can provide earlier assessment of therapy response by observing alterations in perfusion, oxygenation and metabolism. For example, $^{18}$F-FDG PET uses radiolabelled glucose analogue molecules to assess tissue metabolism. Tumors typically have an elevated uptake of glucose, a change in value corresponding to a decrease in tumor tissue metabolism indicates a reduction in tumor load. Similar imaging techniques are disclosed in Kang et al., Korean J. Radiol. (2012) 13(4) 371-390.

In embodiments, reducing tumor size reduces ACTH secretion, or reduces secretion of other hormones, from the pituitary tumor. ACTH or other hormone secretion may be measured, e.g., by sampling blood from the inferior petrosal sinus. In embodiments, reduced tumor size that reduces ACTH secretion from the pituitary tumor will lead to reduced cortisol levels, which can be measured, for example, in blood samples obtained from the patient (either plasma or serum); from urine (e.g., urinary free cortisol); or from saliva.

EXAMPLES

The following examples are provided by way of illustration only and not by way of limitation. Those of skill in the art will readily recognize a variety of noncritical parameters which could be changed or modified to yield essentially similar results.

The following examples show the results of relacorilant administration to patients suffering from pituitary tumors. Relacorilant was well tolerated in clinical studies, and has significantly improved glycemic and hypertension control as well as other manifestations of cortisol excess in patients with endogenous hypercortisolism. Two Cushing's Disease patients treated with relacorilant exhibited significant pituitary tumor shrinkage after three months of daily relacorilant administration.

Example 1

A 50 year old female patient suffering from a pituitary macroadenoma measuring 10 millimeters (mm)×6.3 mm (measurements made by magnetic resonance imaging (MRI)) exhibited cushingoid features (moon face, dorsal fat, supraclavicular fat, plethora, central obesity, facial rubor, easy bruising, abdominal striae) upon medical examination. Biochemical tests indicated hypercortisolism and were consistent with, and confirmatory of, a diagnosis of Cushing's Disease (ACTH 12.2 pmol/L (normal range (NR) 1.3-11.1 pmol/L); late-night serum cortisol (LNSC) 2.25 nmol/L (NR≤2.5 nmol/L), urinary free cortisol (UFC) 177.7 nmol/d (11.1-138 nmol/d); dexamethasone suppression test (DST) 156 ng/mL (15.6 mcg/dL). A MRI image including the patient's pituitary was taken prior to beginning relacorilant treatment (FIG. 1A).

The patient was administered relacorilant for 3 months prior to her previously scheduled transsphenoidal pituitary surgery. Relacorilant was administered to the patient in the morning prior to her morning meal (i.e., in the fasted state). For the first four weeks of relacorilant administration, the daily dose was 100 milligrams (mg) per day of relacorilant administered orally in the morning. For the second four weeks of relacorilant administration, the daily dose was 150 mg per day of relacorilant administered orally in the morning. For the third four weeks of relacorilant administration, the daily dose was 200 mg per day of relacorilant administered orally in the morning.

Figure 1B:
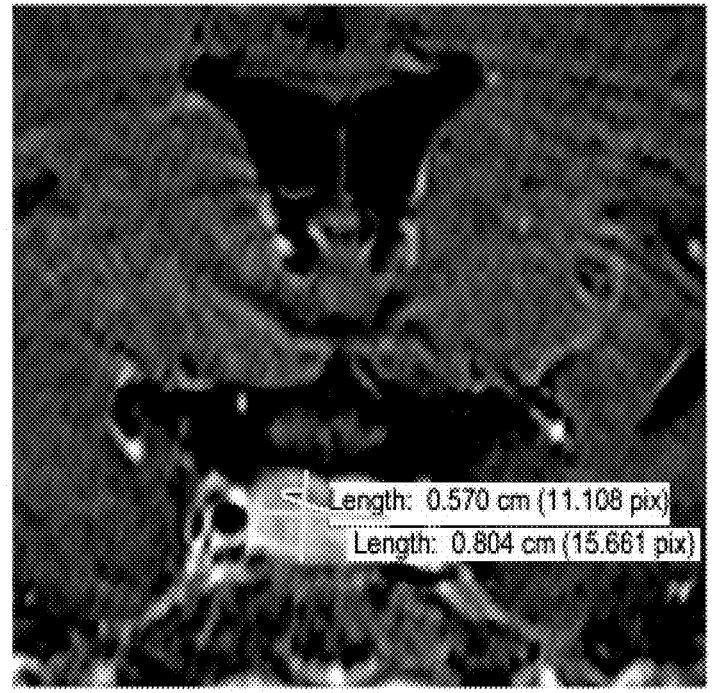
FIG. 1B shows a subsequent coronal MRI image from the same pituitary Cushing's syndrome patient of FIG. 1A. This image shows a cross-section of the patient's macroadenoma following three months of treatment with relacorilant. As shown, following this treatment, the macroadenoma had shrunk, and had dimensions of 0.570 cm (11.108 pixels) by 0.804 cm (15.661 pixels). (This image is enlarged relative to the image of FIG. 1A, as can be seen by the relative sizes of the lateral ventricles.)
Figure 2A:
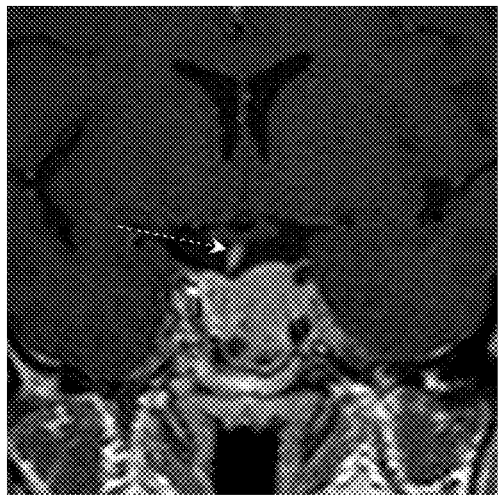
FIG. 2A shows a coronal post-contrast (using a gadolinium contrast agent) MRI image taken at diagnosis of the patient as suffering from pituitary Cushing's syndrome due to a macroadenoma without history of pituitary irradiation. (This patient is discussed in Example 2.) The image shows the patient's macroadenoma having dimensions of 22 by 25 by 26 millimeters (mm) prior to treatment with relacorilant. The dotted arrow indicates displacement of the pituitary stalk away from the centerline.
Figure 2B:
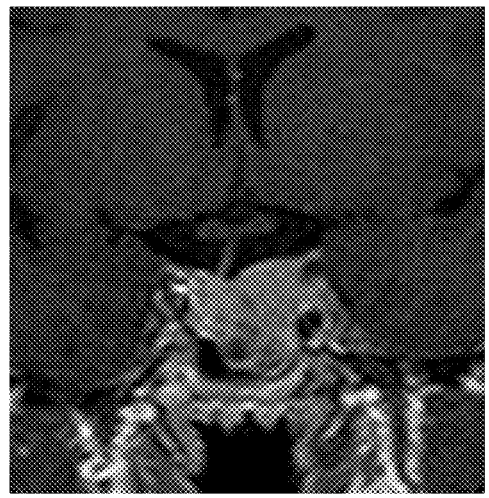
FIG. 2B shows a subsequent coronal MRI image of the patient of FIG. 2A, following treatment with relacorilant, obtained six months after the image of FIG. 2A from the same pituitary Cushing's syndrome patient. Following the treatment, the dimensions of the macroadenoma had shrunk to 21 by 22 by 19 mm.
Figure 2C:
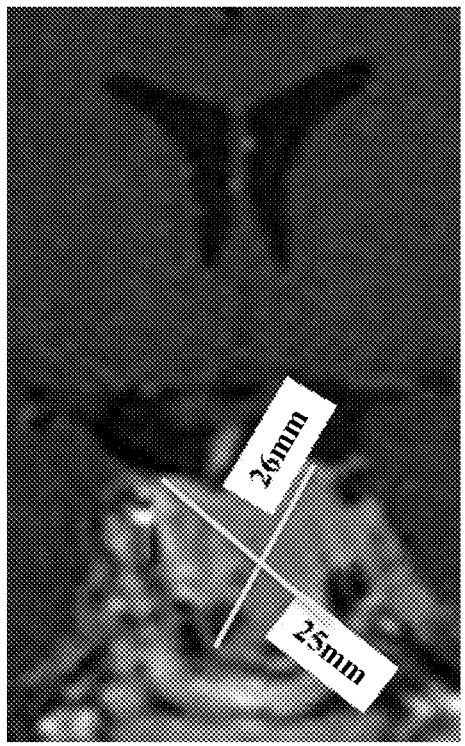
FIG. 2C is the pre-treatment image of FIG. 2A with lines indicating two dimensions of measurement of the tumor. The tumor measured 22 by 25 by 26 millimeters (mm) prior to treatment with relacorilant.
Figure 2D:
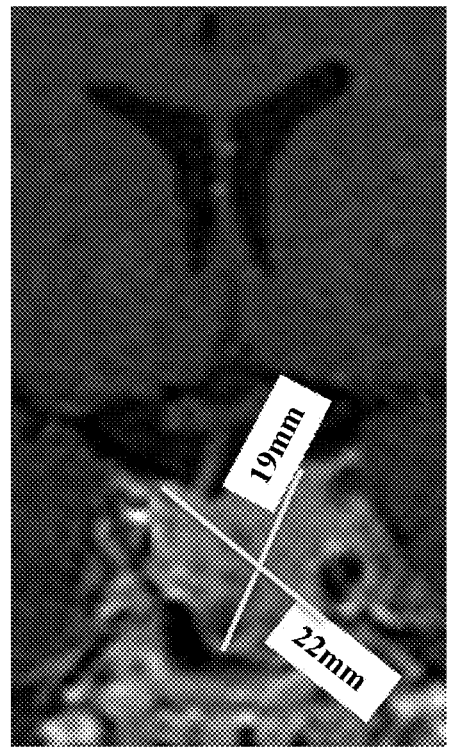
FIG. 2D is the post-treatment image of FIG. 2B with lines indicating two dimensions of measurement of the tumor. The tumor measured 21 by 22 by 19 mm following six months of treatment with relacorilant.

MRI image measurements taken after the 3 months of relacorilant administration and prior to the transsphenoidal pituitary surgery revealed reduction in the size of the tumor as compared to its size prior to relacorilant treatment. The pituitary tumor for this patient decreased from 10 mm×6.3 mm prior to treatment to 8.0 mm×5.7 mm after the three months of treatment with relacorilant. The initial MRI image (prior to relacorilant treatment) for this patient is shown in FIG. 1A. The after-treatment MRI image (after three months of relacorilant treatment) is shown in FIG. 1B.

These MRI images show that the pituitary tumor in this patient was smaller following three months of relacorilant administration than it had been prior to initiation of the relacorilant treatment. The pituitary tumor in this patient shrunk following relacorilant treatment.

Example 2

A 43 year old male patient was found by MRI to have a pituitary macroadenoma measuring 22 millimeters (mm)×25 mm×26 mm. The macroadenoma had a suprasellar extension, and showed invasion of the left cavernous sinus; the MRI further showed that the patient had a right displacement of the pituitary stalk. Medical examination determined that the patient exhibited cushingoid features. Biochemical tests confirmed hypercortisolism and were consistent with Cushing's Disease (ACTH 20.9 pmol/L, (NR 1.3-11.1 pmol/L); LNSC 15.8 nmol/L (NR≤2.5 nmol/L; UFC 356.5 nmol/d (11.1-138 nmol/d); DST 247 ng/mL. (24.7 mcg/dL).

This patient also received relacorilant for 3 months prior to transsphenoidal pituitary surgery for resection of the pituitary macroadenoma. Relacorilant was administered to the patient in the morning prior to his morning meal (i.e., in the fasted state). For the first four weeks of relacorilant administration, the daily dose was 100 milligrams (mg) per day of relacorilant administered orally in the morning. For the second four weeks of relacorilant administration, the daily dose was 150 mg per day of relacorilant administered orally in the morning. For the third four weeks of relacorilant administration, the daily dose was 200 mg, per day of relacorilant administered orally in the morning.

The initial MRI images (prior to relacorilant treatment) for this patient are shown in FIG. 2A, FIG. 2C, FIG. 3A, and FIG. 3C. The after-treatment MRI images (after three months of relacorilant treatment) is shown in FIG. 2B, FIG. 2D, FIG. 3B, and FIG. 3D. The measurements taken from these MRI images (six months after relacorilant treatment, and prior to the patient's transsphenoidal pituitary surgery) demonstrated a reduction in size of the macroadenoma from 22 mm×25 mm×26 mm prior to treatment to 21 mm×22 mm×19 mm after treatment with relacorilant. These MRI measurements demonstrate tumor shrinkage following three months of relacorilant treatment.

Although the tumor is not a cube, so that merely multiplying the measurements in each dimension does not give the true tumor volume, such multiplication of the length measured in each of three orthogonal dimensions provides an indication of the tumor volume. To the extent that such multiplication is indicative of tumor volume, multiplication of the three pre-treatment measurements results in a measure of 14,300 mm³, and multiplication of the three post-treatment measurements results in a measure of 8,778 mm³. Thus, the MRI measurements suggest that the tumor volume shrank by nearly 40% following three months of relacorilant administration.

All patents, patent publications, publications, and patent applications cited in this specification are hereby incorporated by reference herein in their entireties as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

The invention claimed is:

1. A method of reducing the size of a visible pituitary tumor in a patient, the method comprising selecting a patient suffering from a visible pituitary macroadenoma tumor who has not been treated with radiation, said pituitary tumor occupying a location within said patient, said selecting comprising imaging the pituitary tumor effective to determine that the pituitary tumor is a visible macroadenoma and to determine a first size of the pituitary tumor, and then, for three months, administering to the selected patient an effective amount of relacorilant, where relacorilant is ((R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridin-2-yl)methanone), which has the following structure:

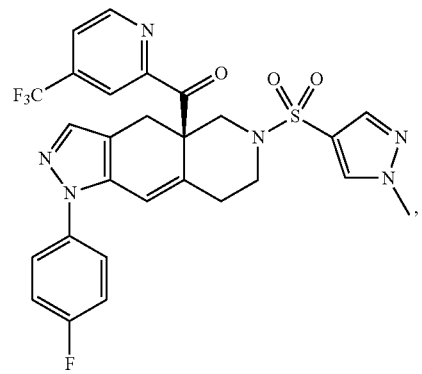 [SMILES: Cn1cc(S(=O)(=O)N2CCC3=Cc4c(cnn4-c4ccc(F)cc4)C[C@]3(C(=O)c3cc(C(F)(F)F)ccn3)C2)cn1]

effective to reduce the size of the pituitary tumor from said first size to a second size, wherein said second size is smaller than said first size following said three months of relacorilant administration.

2. The method of claim 1, wherein said selecting further comprises determining that said patient suffers from a symptom of Cushing's syndrome.

3. The method of claim 1, wherein said patient suffers from Cushing's Disease.

4. The method of claim 1, further comprising measuring said pituitary tumor following relacorilant administration, wherein said measuring comprises a second imaging of the pituitary tumor, and wherein said size is reduced by at least about 27%.

5. The method of claim 1, wherein said relacorilant administration comprises oral administration of relacorilant.

6. The method of claim 1, wherein said pituitary tumor is a non-secreting pituitary tumor.

7. The method of claim 1, wherein said pituitary tumor is a hormone-secreting tumor, and said treatment is effective to reduce the size of the pituitary tumor and to reduce hormone secretion from said pituitary tumor.

8. The method of claim 1, wherein said relacorilant administration comprises daily administration of between about 20 milligrams (mg) to about 800 mg of relacorilant.

9. The method of claim 1, wherein said relacorilant administration comprises daily administration of relacorilant in single unit dosage forms each containing an amount of relacorilant selected from 50 milligrams (mg), 100 mg, 150 mg, 200 mg, 250 mg, 300 mg, 350 mg, 400 mg, 450 mg, and 500 mg of relacorilant.

10. The method of claim 4, further comprising application of a further pituitary tumor targeting treatment following said second imaging of the pituitary tumor.

11. The method of claim 10, wherein said pituitary tumor targeting treatment comprises surgical treatment.

12. The method of claim 5, wherein said administration of relacorilant comprises oral administration of relacorilant to a fasted patient.

13. The method of claim 12, wherein said fasted patient is a patient who has not eaten a meal or otherwise ingested food for at least two hours prior to the administration of relacorilant.

14. The method of claim 5, wherein said administration of relacorilant comprises oral administration of relacorilant to a fed patient.

15. The method of claim 14, wherein said fed patient is a patient who has begun eating a meal about 30 minutes or less prior to the administration of relacorilant.

16. The method of claim 14, wherein a fed patient is a patient who has begun eating a meal about one hour or less prior to the administration of relacorilant.

17. The method of claim 1, wherein said administration of relacorilant comprises relacorilant administration prior to surgery for resection of the pituitary tumor.

18. The method of claim 1, wherein said administration of relacorilant comprises relacorilant administration following surgery for resection of the pituitary tumor.

19. The method of claim 18, wherein said relacorilant administration following surgery for resection of the tumor is effective to reduce the size of, or growth of, tumor tissue remaining in the patient following said surgical treatment.

20. The method of claim 19, further comprising administration of radiation treatment or cancer chemotherapy treatment, or both, to said patient receiving relacorilant administration following surgery for resection of the tumor.

21. The method of claim 1, wherein said administration of relacorilant comprises relacorilant administration to a patient who has been administered another pharmaceutical or medical treatment prior to, or at the same time as, said relacorilant administration.

22. The method of claim 1, wherein said administration of relacorilant comprises relacorilant administration to a patient, followed by surgical treatment to resect said pituitary tumor, then followed by further relacorilant administration.

23. The method of claim 1, wherein said administration of relacorilant comprises relacorilant administration to a patient, followed by surgical treatment to resect said pituitary tumor, then followed by radiation treatment targeting the pituitary tumor and/or regions near the location previously occupied by said pituitary tumor.

24. The method of claim 5, wherein said administration of relacorilant comprises relacorilant administration to a patient, followed by surgical treatment to resect said pituitary tumor, then followed by further relacorilant administration.

25. The method of claim 5, wherein said administration of relacorilant comprises relacorilant administration to a patient, followed by surgical treatment to resect said pituitary tumor, then followed by radiation treatment targeting the pituitary tumor and/or regions near said location previously occupied by said pituitary tumor.

26. The method of claim 14, wherein said administration of relacorilant comprises relacorilant administration to a patient, followed by surgical treatment to resect said pituitary tumor, then followed by further relacorilant administration.

27. The method of claim 14, wherein said administration of relacorilant comprises relacorilant administration to a patient, followed by surgical treatment to resect said pituitary tumor, then followed by radiation treatment targeting the pituitary tumor and/or regions near said location previously occupied by said pituitary tumor.

28. The method of claim 1, wherein said pituitary tumor is hormone-secreting tumor, and said tumor secretes a hormone selected from adrenocorticotrophic hormone, prolactin, growth hormone, thyroid stimulating hormone, follicle stimulating hormone, luteinizing hormone, melanocyte stimulating hormone, β-lipotropin, oxytocin, and vasopressin.

29. The method of claim 5, wherein said pituitary tumor is hormone-secreting tumor, and said tumor secretes a hormone selected from adrenocorticotrophic hormone, prolactin, growth hormone, thyroid stimulating hormone, follicle stimulating hormone, luteinizing hormone, melanocyte stimulating hormone, β-lipotropin, oxytocin, and vasopressin.

30. The method of claim 7, wherein said pituitary tumor is hormone-secreting tumor, and said tumor secretes a hormone selected from adrenocorticotrophic hormone, prolactin, growth hormone, thyroid stimulating hormone, follicle stimulating hormone, luteinizing hormone, melanocyte stimulating hormone, β-lipotropin, oxytocin, and vasopressin.

* * * * *